(12) United States Patent
Finnestad

(10) Patent No.: US 8,727,162 B2
(45) Date of Patent: May 20, 2014

(54) INTEGRAL TORTUOUS PATH RECEPTACLE COVER

(75) Inventor: M. Brian Finnestad, Huntley, IL (US)

(73) Assignee: Covidien AG (CH)

( * ) Notice: Subject to any disclaimer, the term of this patent is extended or adjusted under 35 U.S.C. 154(b) by 814 days.

(21) Appl. No.: 12/480,840

(22) Filed: Jun. 9, 2009

(65) Prior Publication Data

US 2009/0289064 A1 Nov. 26, 2009

Related U.S. Application Data

(63) Continuation of application No. 11/099,072, filed on Apr. 5, 2005, now abandoned.

(51) Int. Cl.
*B65D 51/18* (2006.01)
*B65D 51/04* (2006.01)

(52) U.S. Cl.
USPC ............ 220/254.3; 220/254.1; 220/810; 220/786; 232/47; 232/44

(58) Field of Classification Search
CPC ...... B65D 43/14; B65D 43/16; B65D 43/161; B65D 43/162; B65D 2543/00296; B65D 2251/105; B65D 2251/1058; A61M 5/3205; A61B 19/0288
USPC .......... 220/908, 264, 229, 254.1, 254.3, 810, 220/839, 786, 785; 206/364–366, 370; 232/47, 44, 1 R, 57, 43.1, 43.2; 235/98 R
See application file for complete search history.

(56) References Cited

U.S. PATENT DOCUMENTS

| | | | |
|---|---|---|---|
| 2,990,113 A * | 6/1961 | Fosbrink et al. | 232/7 |
| 4,407,427 A | 10/1983 | Reuter | |
| 4,428,497 A | 1/1984 | Julius et al. | |
| 4,739,900 A | 4/1988 | Borst | |
| 4,874,103 A | 10/1989 | Quisenberry et al. | |
| 4,930,631 A | 6/1990 | Bruno | |
| 5,080,251 A | 1/1992 | Noack | |
| 5,178,322 A | 1/1993 | Shillington | |

(Continued)

FOREIGN PATENT DOCUMENTS

| | | |
|---|---|---|
| EP | 0541339 | 5/1993 |
| EP | 0697344 | 2/1996 |
| EP | 1442723 | 8/2004 |

OTHER PUBLICATIONS

European Search Report dated Jun. 13, 2006, application No. EP 06 00 5426.

(Continued)

*Primary Examiner* — Steven A. Reynolds
*Assistant Examiner* — Javier A Pagan
(74) *Attorney, Agent, or Firm* — Lisa E. Winsor, Esq.

(57) ABSTRACT

A cover for a medical waste disposal receptacle and a method of manufacturing a cover for a medical waste disposal receptacle. The cover generally comprises a body portion configured to substantially close an open end of the receptacle and a lid portion hingedly interconnected to the body portion via an integrally formed hinge extending between the lid portion and a portion of the body portion. The body portion includes a covering surface with an access opening therethrough and at least a first, fixed sloped slide surface depending from the covering surface configured to provide a fixed tortuous path extending from the access opening.

14 Claims, 9 Drawing Sheets

(56) References Cited

U.S. PATENT DOCUMENTS

| | | | |
|---|---|---|---|
| 5,277,312 A | 1/1994 | Vumbaca | |
| 5,322,164 A | 6/1994 | Richardson et al. | |
| 5,387,735 A | 2/1995 | Ponsi et al. | |
| 5,413,243 A | 5/1995 | Bemis et al. | |
| 5,415,315 A * | 5/1995 | Ramirez | 220/345.2 |
| 5,474,180 A | 12/1995 | Robinson et al. | |
| 5,494,186 A | 2/1996 | Marsh | |
| 5,570,783 A | 11/1996 | Thorne et al. | |
| 5,630,506 A | 5/1997 | Thorne et al. | |
| 5,637,099 A * | 6/1997 | Durdin et al. | 604/192 |
| 5,647,502 A | 7/1997 | Marsh | |
| 5,657,894 A * | 8/1997 | Bowen | 220/837 |
| 5,848,692 A | 12/1998 | Thorne et al. | |
| 5,857,569 A * | 1/1999 | Hoftman et al. | 206/366 |
| 5,947,285 A | 9/1999 | Gaba et al. | |
| 5,967,317 A | 10/1999 | Wright | |
| 6,250,465 B1 | 6/2001 | Daniels et al. | |
| 6,409,044 B1 | 6/2002 | Brown et al. | |
| 6,561,352 B2 | 5/2003 | Sherman et al. | |
| 6,732,873 B2 | 5/2004 | Bried et al. | |

OTHER PUBLICATIONS

SharkSafety Brochure, Tyco Healthcare/Kendell, Dec. 2000.

* cited by examiner

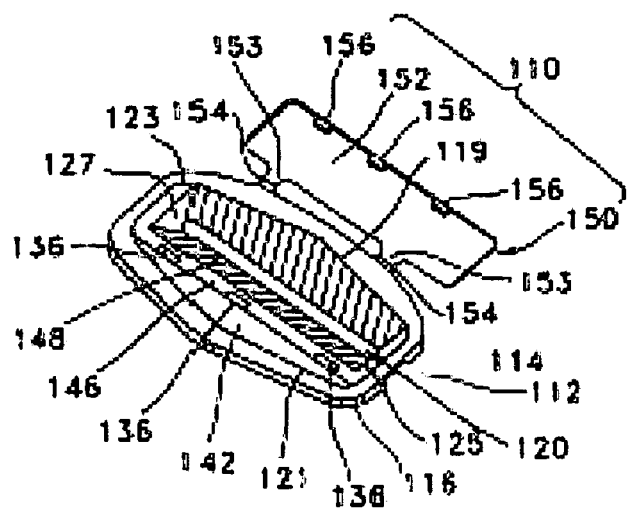
FIG.12
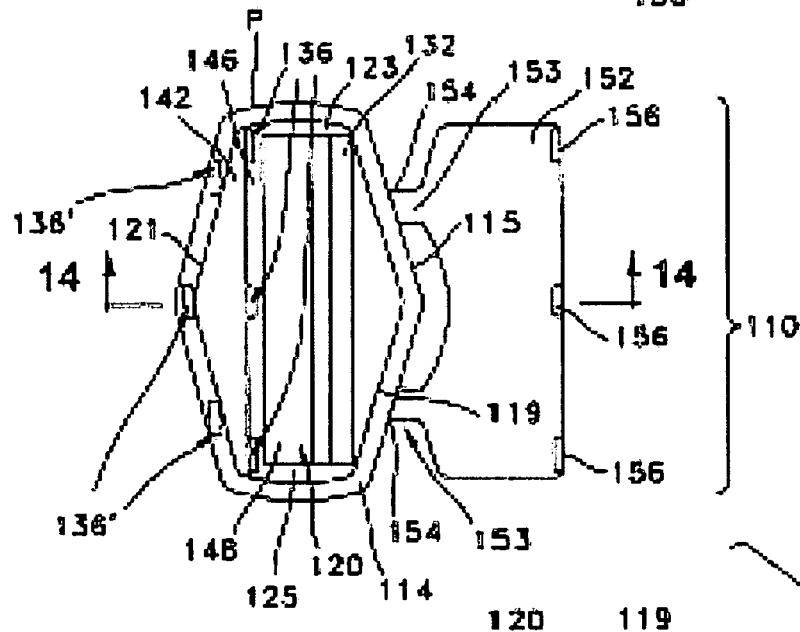
FIG.13
FIG.14

INTEGRAL TORTUOUS PATH RECEPTACLE COVER

CROSS-REFERENCE TO RELATED APPLICATIONS

The present application is a Continuation of co-pending U.S. patent application Ser. No. 11/099,072, filed on Apr. 5, 2005.

BACKGROUND OF THE INVENTION

The present invention relates to a cover for a medical waste disposal receptacle and a method of manufacturing a cover for a medical waste disposal receptacle. More specifically, the present invention relates to medical waste disposal receptacles having a flexibly pivoted top closure lid and, more particularly, to a receptacle cover having an integral pivoted lid portion and a body portion having an integral tortuous path access opening.

Various types of containers for hospital use have been developed for receiving medical waste in a surgical operating room, pre-op or post-op room, a patient's room, or in other clinical or non-clinical settings in which medical waste is generated. These containers are particularly designed to protect the user of such containers, such as doctors, nurses, or other hospital personnel, from the hospital waste products that may be disposed therein. Such hospital waste products might include surgical sharps, such as needles, syringes, scalpel blades, or the like, or might include gauzes, bandages, or sponges. It is important to prevent the user of a sharps container from being accidentally cut or punctured by its contents.

Examples of such containers include those shown in U.S. Pat. No. 5,058,764, entitled "Mounting Bracket Having A Hidden Lock For A Sharps Collection System"; U.S. Pat. No. 5,080,251, entitled "Tortuous Path In-Patient Room Medical Waste Disposal Container"; and U.S. Pat. No. 5,494,186, entitled "Wall Mounted Medical Waste Disposal Container With Pivoted Top Closure Lid."

While the prior art containers provide a desired level of protection, they generally require various components to be formed separately and thereafter assembled. These additional steps add cost and complexity to the manufacturing process.

SUMMARY OF THE INVENTION

In at least one embodiment, the cover comprises a body portion configured to substantially close an open end of the receptacle. The body portion has a given perimeter and defines a tortuous path access opening. A lid portion configured to selectively close the access opening is hingedly interconnected to the body portion via an integrally formed hinge extending between the lid portion and a portion of the body portion given perimeter.

In at least one embodiment, the cover comprises a body portion including a covering surface configured to substantially close the receptacle open end. The body portion further includes first and second slide surfaces depending from the covering surface. The first and second slide surfaces are axially spaced in non-overlapping relation to define a tortuous path access opening through the covering surface.

In at least one embodiment, the receptacle includes an open end and a receptacle body having an axis extending from the open end in a given direction and the cover comprises a body portion configured to substantially close the open end of the receptacle. The body portion defines a tortuous path access opening having opposed, axially spaced, first and second lateral edges. The body portion includes at least a first integral slide surface that defines the first lateral edge. The first and second lateral edges are configured such that a plane extending through the first and second lateral edges is at an angle of between 0 degrees and about 20 degrees relative to a plane parallel to the given direction and extending through the second lateral edge.

The method, according to one exemplary embodiment, comprises the steps of disposing a moldable material in a linearly separable mold assembly having one or more cavities configured to define the tortuous path receptacle cover, and removing the integrally formed cover from the mold assembly.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 12 is a top, front isometric view of a cover that is a second embodiment of the present invention.

FIG. 13 is a top plan view of the cover of FIG. 12.

FIG. 14 is a cross-sectional side view along the line 14-14 in FIG. 13.

DETAILED DESCRIPTION OF THE INVENTION

Figure 1:
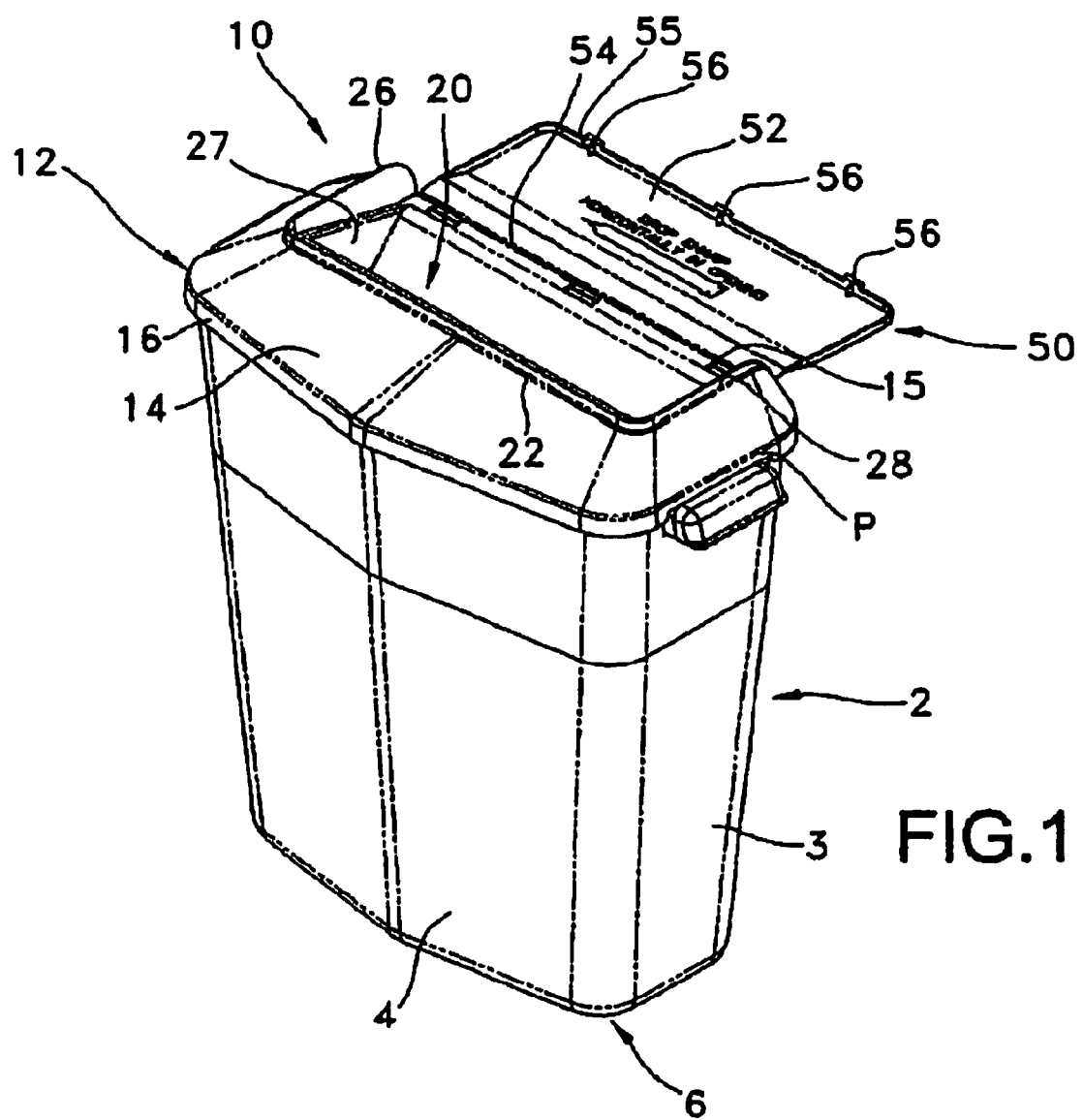
FIG. 1 is a top, front isometric view of a cover that is a first embodiment of the present invention positioned on an illustrative receptacle.

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose of illustration. The invention is not limited to any particular dimensions, materials, or other details of the illustrated embodiments.

Figure 2:
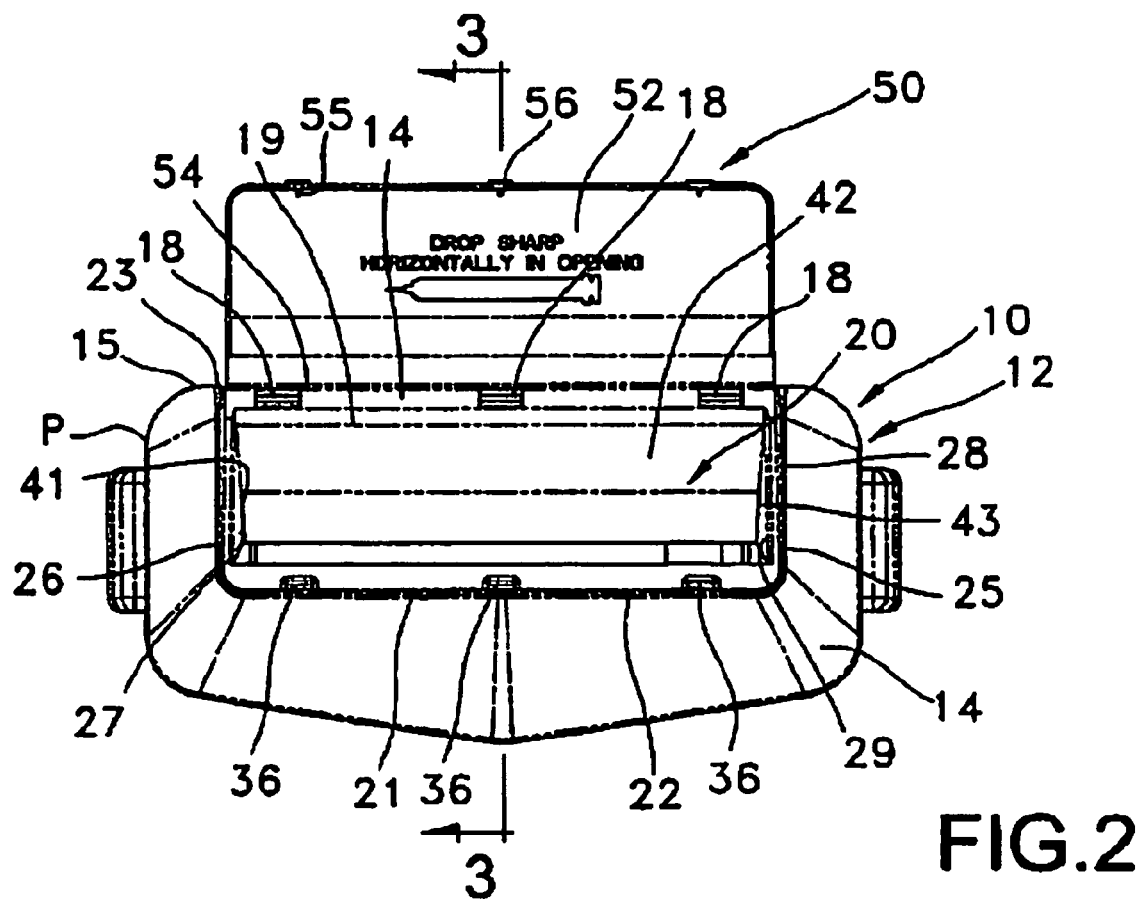
FIG. 2 is a top plan view of the cover of FIG. 1.
Figure 3:
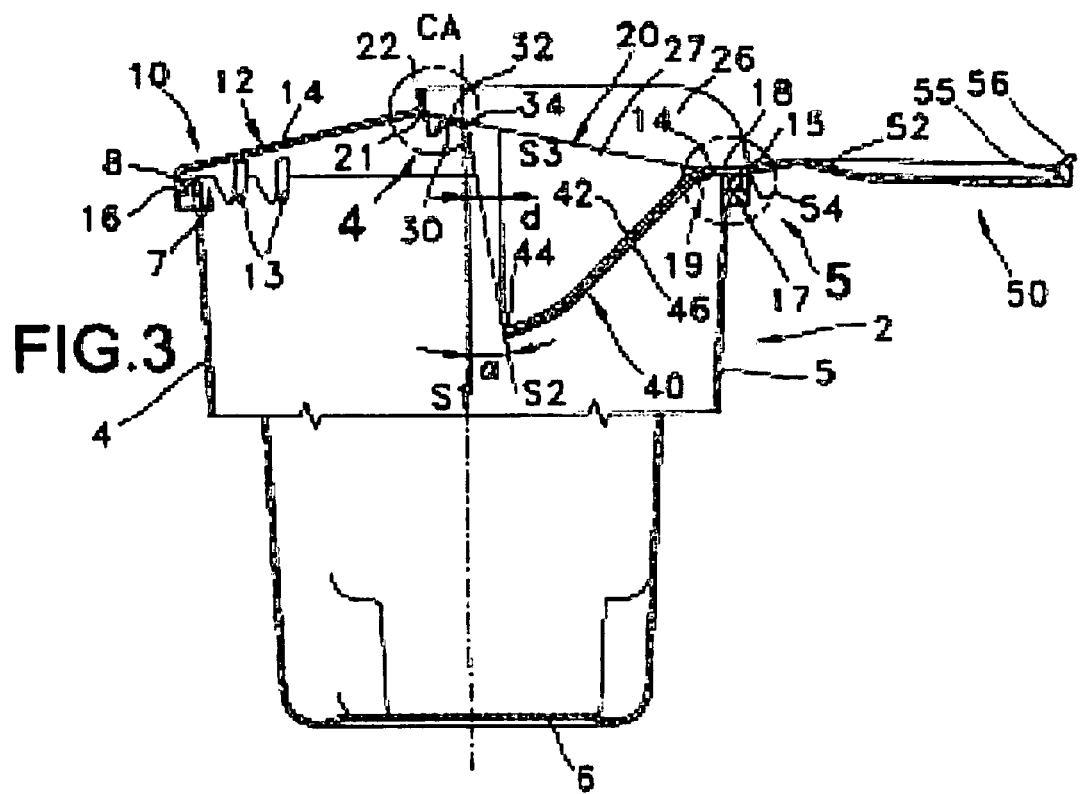
FIG. 3 is a cross-sectional view along the line 3-3 in FIG. 2.

Referring to FIGS. 1-7, a cover 10 that is a first embodiment of the present invention will be described. The cover 10 is configured to be positioned on a medical waste disposal receptacle 2. The receptacle 2 generally includes a body defined by a front wall 4, a pair of side walls 3, and a rear wall 5 extending from a base 6. The walls 3, 3, 4 and 5 define a generally open end 7 opposite the base 6. The open end 7 defines a rim 8 about its perimeter. The rim 8 may have various configurations. As shown in FIG. 3, the edges of the walls 3, 3, 4 and 5 are curled over to define the rim 8, however, a curl is not required and other configurations may be utilized.

The walls 3, 3, 4 and 5 are generally planar surfaces, but may have various configurations. For example, the front wall 4 in the present embodiment defines a chevron shape. In the present embodiment, the rear wall 5 is a substantially planar surface which allows the receptacle to be positioned against a wall or the like. The receptacle 2 has a central axis CA extending from the base 6 to the open end 7. The receptacle 2 is typically positioned in use in a vertical position with the central axis CA extending vertically. In this typical arrangement, the open end 7 extends along a horizontal plane. Other configurations of the receptacle 2 and other mounting arrangements may also be utilized.

The cover 10 generally comprises a body portion 12 and a lid portion 50. The body portion 12 includes a covering surface 14 configured to substantially cover and thereby close the receptacle open end 7. The covering surface 14 generally has a configuration that complements the configuration of the receptacle rim 8. As such, in the present embodiment, the covering surface 14 has a front portion with a chevron shape and a rear portion that is shaped to correspond to the planar rear wall 5.

Figure 4:
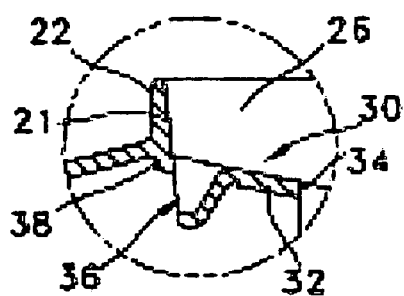
FIG. 4 is a detailed view of a lock portion of the cover as denoted in FIG. 3.
Figure 5:
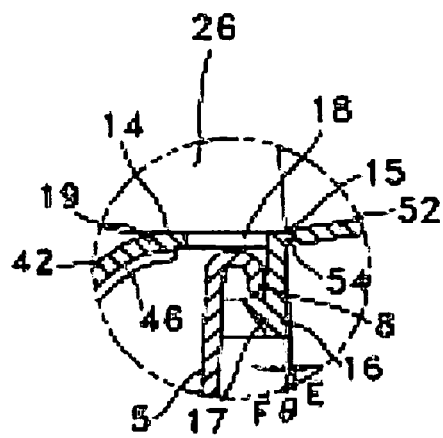
FIG. 5 is a detailed view of a hinge portion of the cover as denoted in FIG. 3.
Figure 6:
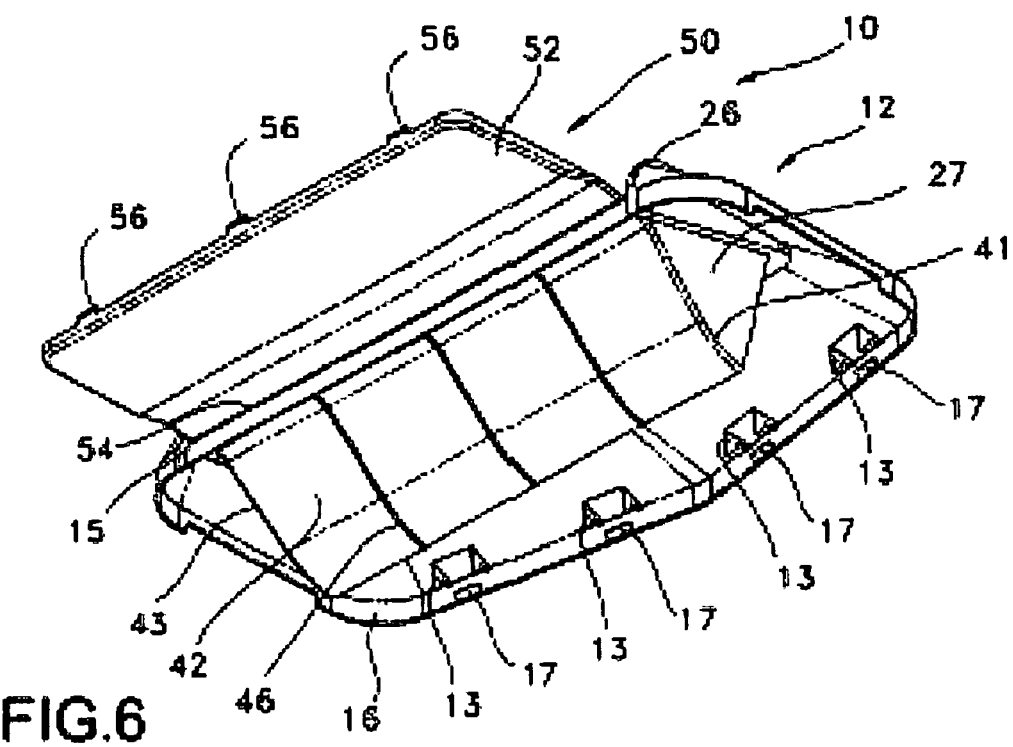
FIG. 6 is a bottom, front isometric view of the cover of FIG. 1.

A flange 16 depends from at least a portion of the covering surface 14. The flange 16 is configured to fit about the receptacle open end rim 8. The flange 16 may be continuous about the perimeter of the receptacle rim 8 (as in the embodiment of cover 10 illustrated in FIGS. 1-7), or may be segmented and provided at various positions about the receptacle rim 8. The body portion 12 is preferably provided with means for securing the cover 10 to the receptacle 2. In the present embodiment, locking tabs 17 configured to engage the receptacle rim 8 are provided at various locations about the flange 16, as shown in FIG. 5. Alternatively, the body portion 12 may have a friction fit with respect to the receptacle 2, clips (not shown) may extend between the body portion 12 and the receptacle 2, the receptacle rim 8 may be provided with projections which engage the flange 16, or the body portion 12 may be provided with projections which extend through bores provided in the receptacle rim 8. Other securing means may also be utilized. The body portion 12 may further include internal ribs 13 configured to engage the receptacle 2 to further support the cover 10 relative to the receptacle 2.

The body portion 12 has an access opening 20 through the covering surface 14. The access opening 20 is positioned within an inlet area that is defined by a rear lateral edge 19, a front lateral edge 21 and opposed side edges 23 and 25 extending between the rear and front edges 19, 21. A front wall 22 is provided along the front lateral edge 21 and opposed side walls 26, 28 extend along the side edges 23, 25, respectively. The lid portion 50 extends proximate to the rear edge 19 as will be described in greater detail hereinafter.

Figure 7:
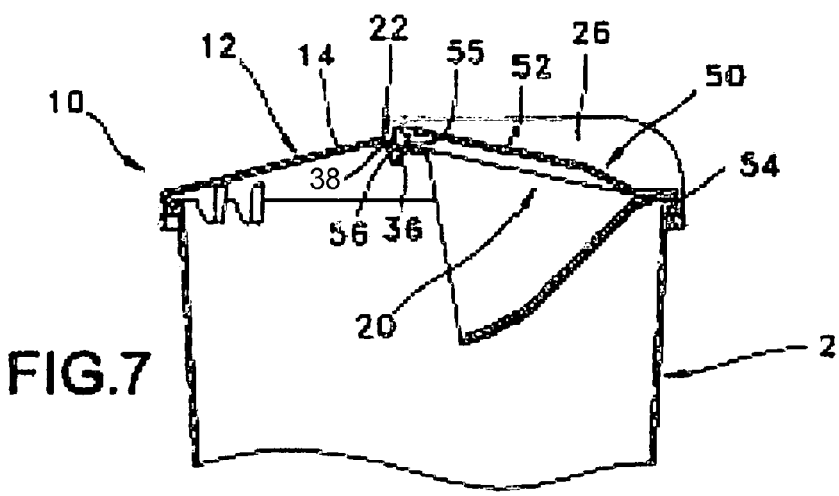
FIG. 7 is a cross-sectional view similar to FIG. 3 showing a lid portion in a closed position.
Figure 8:
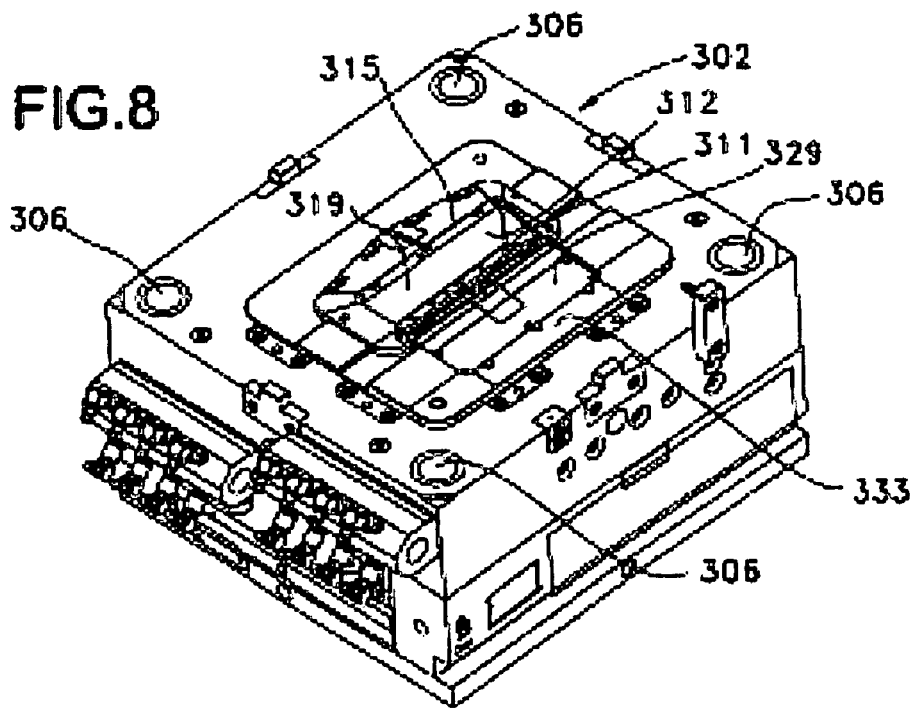
FIG. 8 is an isometric view of a first portion of an embodiment of a mold assembly utilized to manufactured the cover of FIG. 1.
Figure 9:
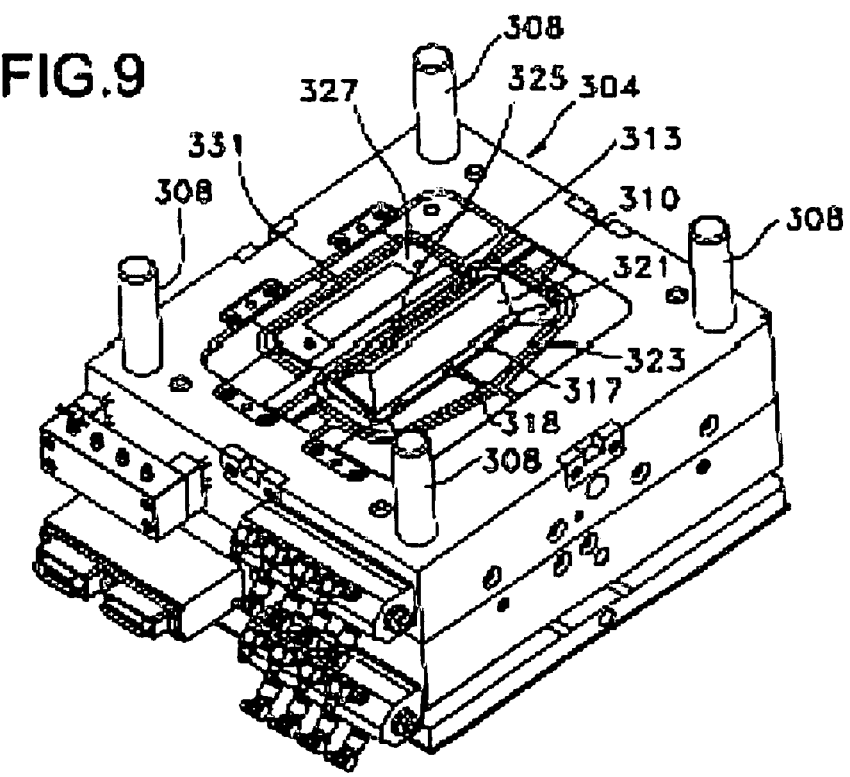
FIG. 9. is an isometric view of a second portion of the mold assembly utilized to manufactured the cover of FIG. 1.

As shown in FIGS. 3 and 7, the side walls 26, 28 may extend beyond the access opening edges 23, 25 to the location of a hinge 54 of the lid portion 50. In use, the receptacle 2 is secured to a wall surface or the like with the lid portion 50 pivoted to a substantially vertical or upwardly-angled position in which the lid portion 50 rests against the wall surface. The lid portion 50 may have instructions inscribed on an internal surface that will be directed to a user when the lid portion 50 is in this use position. For example, the lid portion 50 optionally includes directions such as "DROP SHARP HORIZONTALLY IN OPENING," other information, or other indicia for communication to a user of the cover 10.

In this use position, the lid portion 50, the opening front wall 22 and the opening side walls 26, 28 effectively define a funnel into the access opening 20. Any sharp or other device positioned within this funnel area will thereby be directed to the access opening 20. Referring to FIG. 1, the covering surface 14 slopes downward from the opening front wall 21 and the opening side walls 26, 28 to the perimeter P. As such, the sloped covering surface 14 is not configured to accommodate a sharp or other device. This configuration discourages a user from intentionally or inadvertently leaving a sharp or the like on the covering surface 14 which may pose a danger to that user or a later user.

Referring to FIG. 3, a substantially fixed tortuous path extends from the inlet area defined by the rear lateral edge 19, the front lateral edge 21 and the opposed side edges 23 and 25 and through the access opening 20 to provide a tortuous entry passage into the receptacle cavity. The tortuous entry passage allows for the unrestricted passage of medical instruments and/or waste past stationary surfaces while making hand insertion into the receptacle difficult, if not impossible. In the present embodiment, the tortuous path is defined by a front slide 30 extending from the front lateral edge 21 and a rear slide 40 extending from the rear lateral edge 19. The front and rear slides 30, 40 are formed integrally with the covering surface 14. Preferred methods of manufacture are described in more detail hereinafter.

The front slide 30 includes a sloped front slide surface 32 terminating along a lateral edge 34. The front slide surface 32 extends laterally between the opposed side walls 26, 28 and has a generally planar configuration, although other configurations are possible. The rear slide 40 includes a sloped rear slide surface 42 terminating along a lateral edge 44. The rear slide surface 42 has a curved surface that reduces in slope toward the lateral edge 44. Other configurations are also possible. The rear slide surface 42 extends laterally between rear slide surface edges 41 and 43 as shown in FIG. 2. Each side wall 26, 28 includes or extends to an extending wall portion 27, 29, respectively, extending from the side wall 26, 28 to the respective slide surface edge 41, 43. The extending wall portions 27, 29 extend between the rear edge 19 and the front slide surface lateral edge 34, but may extend farther.

The extending wall portions 27, 29 retain deposited materials within the lateral extents of the rear slide surface 42 and also provide support for the rear slide surface 42 of rear slide 40. A substantially rectangular lower opening is therefore defined by the lateral edge 44 of the rear slide surface 42 and the forward edges of the extending wall portions 27, 29. This lower opening is oriented in a plane that is substantially vertical or at an angle to a vertical plane, as will be described later in greater detail. Supporting ribs 46 or the like may be provided along a rear surface of the rear slide 40, on or opposite rear slide surface 42, at various locations between the side edges 41, 43 to provide additional support.

The perimeter edge of the access opening 20 is therefore defined by the rear lateral edge 19, the front lateral edge 34 and upper edges of the extending wall portions 27, 29. Thus, a substantially rectangular access opening 20 (in the embodiment illustrated in FIGS. 1-7) is oriented along a plane that is sloped toward the rear of the cover 10.

Medical waste introduced into the tortuous path through the inlet area of the cover 10 follows a circuitous path into the interior of the receptacle 2. More specifically, medical waste is deposited within the interior of the receptacle 2 after it passes into the inlet area defined by the rear lateral edge 19, front lateral edge 21 and opposed side edges 23 and 25; travels through the access opening 20 defined by the rear lateral edge 19, the front lateral edge 34 and upper edges of the extending wall portions 27, 29; and passes through the lower opening defined by the lateral edge 44 of the rear slide surface 42 and the forward edges of the extending wall portions 27, 29.

The front slide 30 and the rear slide 40 are configured such that the front slide surface 32 is horizontally axially spaced from the rear slide surface 42 in non-overlapping relation. More specifically, a plane S1 parallel to the central axis CA and extending through the front lateral edge 34 of the front slide surface 32 is horizontally axially spaced a distance d from a plane S3 parallel to the central axis CA and extending through the lateral edge 44 of the rear slide surface 42. The distance d is from 0 inches to approximately 1 inch, with a preferred range from greater than zero inches to about 7/8 inch, and a more preferred range from about 1/8 inch to about 5/8 inch, and a more preferred range from about 1/4 inch to about 1/2 inch. Additionally, a plane S2 extending through the front lateral edge 34 of the front slide surface 32 and the lateral edge 44 of the rear slide surface 42 (i.e., the plane of the lower opening defined by the lateral edge 44 of the rear slide surface 42 and the forward edges of the extending wall portions 27, 29) is at an angle .alpha. relative to the plane S1. The angle .alpha. is from 0 degrees to approximately 25 degrees, with a preferred range from greater than 0 degrees to about 20 degrees, and a more preferred range from about 2 degrees to about 15 degrees, and a more preferred range from about 5 degrees to about 10 degrees. The distance d and the angle .alpha. are selected to provide a tortuous path entry passage having a desired waste clearance and a desired user inaccessibility.

The substantially fixed tortuous path allows a user to dispose of an item into the receptacle 2 by dropping the item into the funnel area leading to the access opening 20. Gravity causes the item to pass by the front and rear slides 30, 40 and into the receptacle 2. The user does not have to actuate the cover 10 to cause disposal or even contact the cover 10 in any manner during disposal. The disposed item passes freely into the receptacle 2, however, the tortuous path reduces or eliminates the possibility of an individual reaching into the receptacle 2.

While the present embodiment is described with a front slide 30 and a rear slide 40, both may not be necessary. For example, the front slide 30 may be eliminated while the rear slide surface 42 is extended axially in a forward direction. With the front slide 30 eliminated, the plane S1 would extend through the opening front edge 21. If so modified, the spatial relationship between the planes S1 and S3 and the angular relationship between planes S2 and S1 provided in the cover 10 would still be maintained to provide a desired tortuous path.

Additionally, while the present embodiment is described with the rear slide surface 42 having a larger axial length than the front slide surface 32, such configuration can be reversed. For example, the front slide surface 32 may be configured with a larger axial length and extending at a steeper angle such that the front lateral edge 34 of the front slide surface 32 is lower than the lateral edge 44 of the rear slide surface 42. Other configurations may also be utilized.

To close the access opening 20 once the receptacle is filled to a desired level, the cover 10 includes a lid portion 50 configured to cover and close the inlet area and access opening 20. In the present embodiment, the lid portion 50 is integrally hinged to the body portion 12 along a rear edge 15 of the outer perimeter P of the body portion 12. The outer perimeter P is defined by the outer extent of the covering surface 14 and the flange 16. The perimeter P may be defined by both the covering surface 14 and the flange 16 if, for example, the flange 16 extends radially outward of the covering surface 14 along a portion of the perimeter, but is inward of the covering surface 14 along other portions of the perimeter. At the locations where the flange 16 is outward, the flange 16 will define that portion of the perimeter P and at locations where the covering surface 14 is outward, the covering surface 14 will define that portion of the perimeter P.

The lid portion 50 includes a lid surface 52 configured to complement the shape of the inlet area and/or the access opening 20. In the present embodiment, the lid surface 52 has a substantially rectangular configuration, but other configurations are also possible. An integral hinge 54 (e.g., a living hinge) extends between the lid surface 52 and the rear perimeter edge 15 of the body portion 12. The hinge 54 of the present embodiment extends substantially along the entire length of the lid surface 52, however, the hinge 54 may be formed as one or more segments that extend less than the length of the lid surface 52. As illustrated in FIG. 5, the hinge 54 is optionally formed by providing a section of reduced material thickness. Such reduced thickness provides the hinge 54 with greater flexibility than the neighboring lid portion 50 or cover portion 10. The hinge 54 therefore has sufficient flexibility to allow the lid portion 50 to be pivoted from the open position shown in FIG. 3 to the closed position shown in FIG. 5, to be described in greater detail later.

To lock the lid portion 50 in the closed position, the lid portion 50 includes one or more locking tabs 56 extending from the lid surface 52. A locking bore 36 corresponding to each locking tab 56 is provided adjacent the opening front edge 21 (FIG. 4). In the present embodiment, the locking bores 36 are provided through the front slide surface 32 and each locking bore 36 defines a locking shoulder 38 below the front wall 22, as shown in FIG. 4. To close the inlet area and access opening 20, the lid surface 52 is pivoted about the hinge 54 until each locking tab 56 engages a respective locking shoulder 38, as shown in FIG. 7. The engagement of the locking tabs 56 with the locking shoulders 38 preferably permanently locks the lid portion 50 in the closed position, prevents unauthorized opening of the lid portion 50, and/or inhibits unintended opening of the lid portion 50. Each locking tab 56 preferably has a support rib 55 having a width equal to the width of the locking bore 36 to prevent prying of the locking tabs 56 from the locking bores 36 (see FIGS. 1-3 and 7).

Having generally described the components of the cover 10 and the operation thereof, a method of manufacturing the cover 10 that is a first embodiment of the inventive method will be described with reference to FIGS. 3, 5 and 8-11. The first embodiment of the inventive method utilizes a mold assembly 300 including first and second mold portions 302, 304 that are linearly moveable relative to each other in a direction parallel to the mold axis MA. The mold assembly 300 is configured for use in an injection molding process in which plastic material is injected into a cavity defined by mold portions 302, 304 to form the cover 10. In use, the mold portions 302, 304 are moved with respect to one another along the mold axis MA between an open position in which the mold portions are spaced from one another (e.g., for removal for a completed cover 10) and a closed position in which the mold portions contact one another to define the cavity.

The mold portions 302 and 304 have a control assembly for controlling the alignment and movement of the mold portions 302 and 304 relative to one another. For example, one mold portion 304 may be provided with posts 308 that are received in corresponding bores 306 in the other mold portion 302 to align and control linear motion of the mold portions 302 and 304. Other assemblies may also be utilized.

The mold assembly 300 has one or more injection ports 330 or the like configured to dispose moldable material in cavity portions 318, 320, 322, 324, 326 formed between the mold portions 302 and 304. The mold portions 302 and 304 and cavity portions 318, 320, 322, 324, 326 are configured such that all of the components of the cover 10 may be formed as a unitary structure while allowing simple linear separation of the mold portions 302 and 304 in a direction parallel to the mold axis MA, as indicated by arrows A in FIG. 11. In other words, all of the surfaces of the mold cavity forming cover 10 are provided, according to one exemplary aspect of this invention, by two mold portions movable along a common axis. Thus, simplified and cost effective mold tooling and processes are optionally employed, thereby reducing the effort and cost associated with the manufacture of the cover 10. Known mold assemblies, in contradistinction, have required additional mold components, for example, cross sliding components to make complex, unitary structures.

Referring to FIGS. 8-11, both mold portions 302, 304 include male and female mold surfaces 310, 311, 312, 313, 315, 317, 319, 321, 323, 325, 327, 329, 331, 333, 335 configured and positioned to define the cavity portions 318, 320, 322, 324, 326 when the mold portions 302 and 304 are positioned relative to one another. For example, a cavity portion 324 configured to form the rear slide 40 of the cover 10 is defined by mold surfaces 311, 312 and 313 while cavity portion 322 configured to form the front slide 30 of the cover 10 is defined by mold surfaces 310, 315 and 317.

Figure 10:
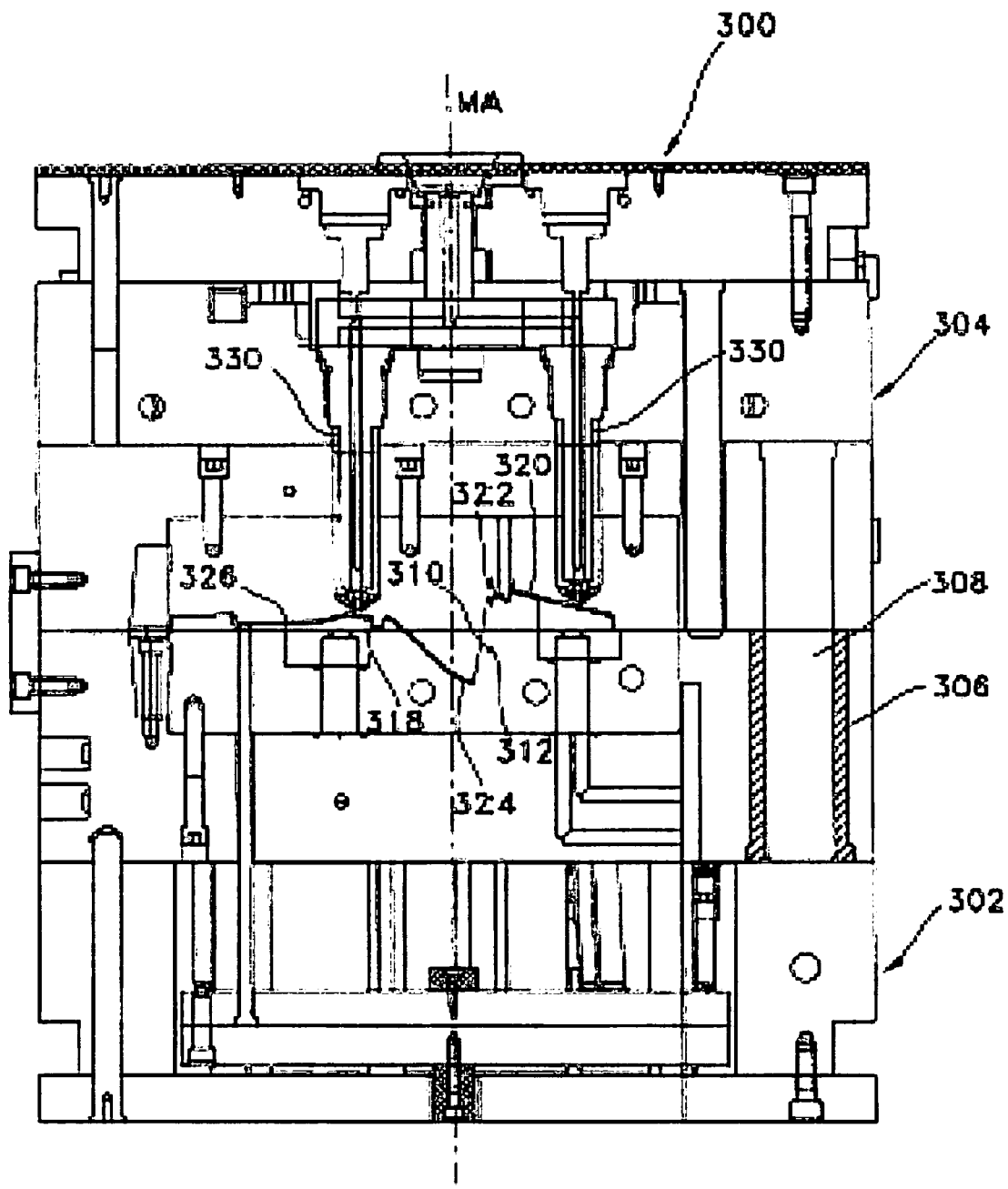
FIG. 10 is a cross-sectional side view showing the first and second mold portions of FIGS. 8 and 9 in an assembled configuration.
Figure 11:
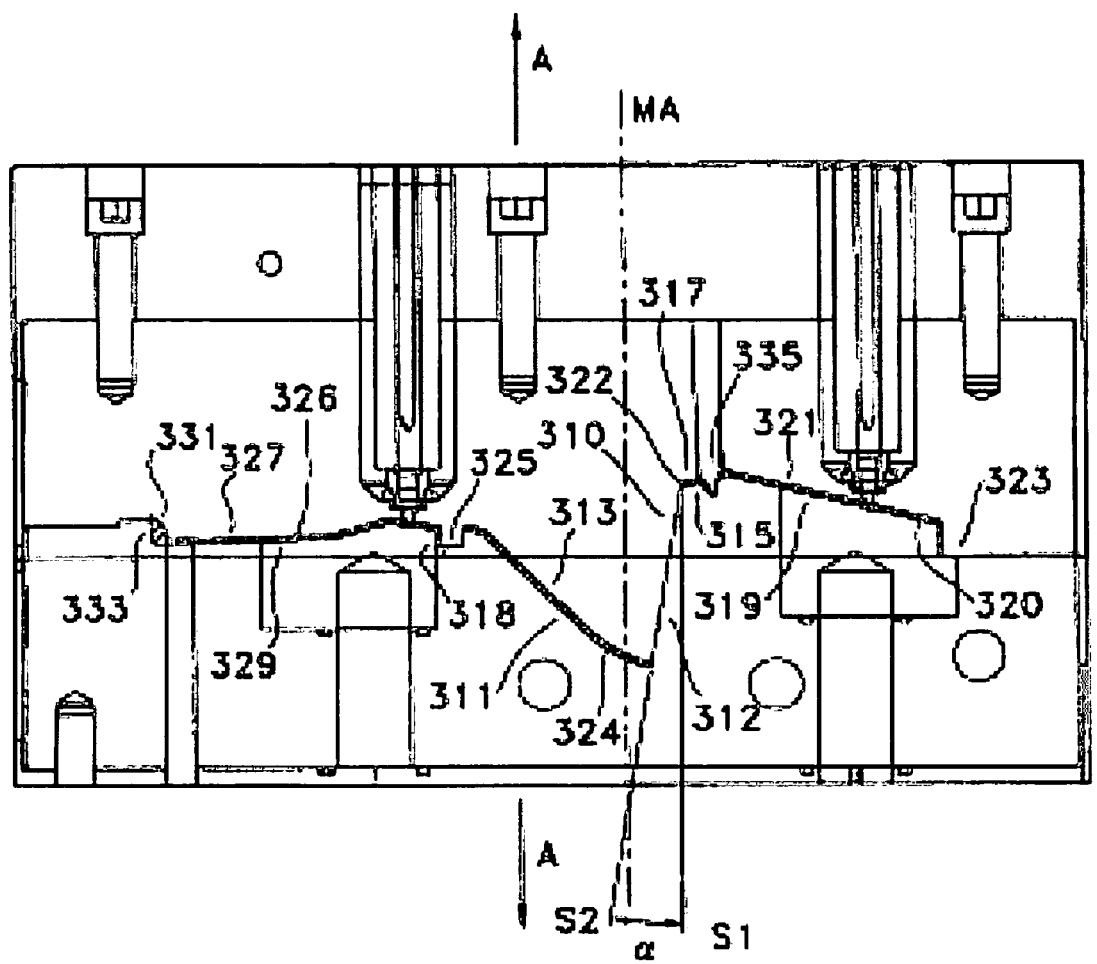
FIG. 11 is a detailed view of the cavity portions of the mold assembly of FIG. 10.

As shown in FIGS. 10 and 11, the mold surfaces 310 and 312 mate along the plane S2, which is the plane that extends through the front lateral edge 34 of the front slide surface 32 and the lateral edge 44 of the rear slide surface 42 of the cover 10 (i.e., the plane of the lower opening defined by the lateral edge 44 of the rear slide surface 42 and the forward edges of the extending wall portions 27, 29). The plane S1 (the plane parallel to the central axis CA and extending through the front lateral edge 34 of the front slide surface 32 of the cover 10) is configured to be substantially parallel to the mold axis MA. The angle .alpha. of the mating plane S2 relative to the plane S1 allows the mold surfaces 310 and 312 to adequately seal between the two cavities 322 and 324. Additionally, the angle .alpha. of the mating plane S2 allows the two mold portions 302 and 304 to be moved apart in a direction parallel to the mold axis MA, as indicated by arrows A, without interfering with either of the molded slide surfaces 32 or 42 that are formed in the cavity portions 322 and 324, respectively. As indicated previously, the angle .alpha. according to one embodiment is between 0 degrees and approximately 20 degrees, with a preferred range from about 2 degrees to about 15 degrees, and a more preferred range from about 5 degrees to about 10 degrees.

Additional mold surfaces 325 may be provided adjacent the surface 313 to assist in forming the locking tabs 17 along the rear portion of the rim 16. As illustrated in FIG. 5, the mold surfaces 325 leave apertures 18 through the covering surface 14; however, the apertures 18 are sufficiently small that they do not allow access within the cover 10 and are also covered by the lid portion 50 when the lid portion 50 is closed as illustrated in FIG. 7. Similarly, mold surfaces 335 may be provided adjacent mold surface 317 to define the locking bores 36 illustrated in FIG. 4. The mold surfaces 335 cooperate with the mold surface 319 to define the locking shoulders 38.

Mold surface 319 also cooperates with mold surfaces 321 and 323 to define cavity portion 320 configured to form the body portion 12. Mold surfaces 327 and 329 cooperate to define cavity portion 326 configured to form the lid surface 52. Mold surfaces 327 and 329 further cooperate with mold surface 325 to define cavity portion 318 configured to form the hinge 54 between the lid surface 52 and the body portion 12. The mold surface 329 is preferably configured to form the flange 16 with an inward draft angle, as indicated in FIG. 5 by the angle .theta. between planes E and F. The inward draft angle assists in defining the hinge cavity portion 318 and the separation of the mold portions 302 and 304. Mold surfaces 327, 331 and 333 cooperate to define a cavity portions configured to form the locking tabs 56.

As illustrated in FIG. 11, the mold surfaces are preferably configured such that the cavity portion 326 that forms the lid portion 50 is at an approximate right angle with respect to the mold axis MA to facilitate separation of the mold portions 302 and 304 in the direction of arrows A. However, other angles may also be utilized.

To form the integral cover 10, moldable material is supplied to the cavity portions, for example, through injection ports 330. The mold portions 302 are thereafter separated in the direction of arrows A in FIG. 11 and the integral cover 10 is removed. The cover 10 is substantially ready for use and does not require any substantial secondary operations to assemble the cover 10.

Referring to FIGS. 12-14, a cover 110 that is alternate embodiment of the present invention will be described. The cover 110 is similar to cover 10 in that it has a one-piece construction that is capable of being formed using a cost effective molding process. As will be describe in detail below, however, the cover 110 differs from cover 10 in the manner in which the lid is coupled to the body portion and in other ways.

The cover 110 includes a body portion 112 and a lid portion 150. The body portion 112 includes a covering surface 114 configured to substantially cover and thereby close a receptacle open end 7. The covering surface 114 generally has a configuration that complements the configuration of the receptacle rim 8. In the present embodiment, the covering surface 114 has a chevron shape in both the front and rear portions.

A flange 116 depends from at least a portion of the covering surface 114. The body portion 112 of cover 110 is preferably provided with means for securing the cover 110 to a receptacle 2. In the present embodiment, locking tabs 117 configured to engage the receptacle rim 8 are provided at various locations about the flange 116, as shown in FIG. 14. Other securing means may also be utilized.

The body portion 112 has an access opening 120 through the covering surface 114. The access opening 120 is defined by a rear lateral edge 119, a front lateral edge 121 and opposed side edges 123 and 125 extending between the rear and front edges 119, 121. Referring to FIG. 14, a substantially fixed tortuous path extends from the access opening 120 to provide a tortuous entry passage into the receptacle cavity from the access opening 120 which allows for the unrestricted passage of medical instruments and/or waste past stationary surfaces while making hand insertion into the receptacle difficult, if not impossible. In the present embodiment, the tortuous path is defined by a rear slide 130 extending from the opening rear lateral edge 119 and a front slide 140 extending from the opening front lateral edge 121. The rear and front slides 130, 140 are formed integrally with the covering surface 114.

The rear slide 130 includes a sloped rear slide surface 132 terminating along a lateral edge 134. The rear slide surface 132 extends laterally between opposed side walls 127 and has a generally planar configuration, although other configurations are possible. The front slide 140 includes a stepped front slide surface terminating along a lateral edge 144. The stepped slide surface includes a first sloped portion 142 followed by a substantially horizontal step 146 followed by a second sloped portion 148 that terminates at the lateral edge 144. The first and second slide surfaces 142 and 148 are substantially planar surfaces, but other configurations are also possible.

The perimeter edge of the access opening 120 is therefore defined by the rear lateral edge 119, the front lateral edge 121 and upper edges of the side walls 127. Thus, a substantially rectangular access opening 120 (in the embodiment illustrated in FIGS. 12-14) is oriented along a plane that is substantially horizontal but that may be sloped such as toward the rear of the cover 110.

The horizontal step 146 of the front slide 140 includes a plurality of locking bores 136 configured to receive locking tabs 156 on the lid portion 150 as will be described hereinafter. The front slide extends laterally between side walls 127. The rear and front slides 130, 140 and the side walls 127 effectively define a funnel-shaped path into the receptacle. A substantially rectangular lower opening is therefore defined by the lateral edge 144 of the front slide surface 142 and the lower edges of the side walls 127. This lower opening is oriented in a plane that is substantially vertical or at an angle to a vertical plane, as will be described later in greater detail.

Medical waste introduced into the tortuous path through the inlet area of the cover 110 follows a circuitous path into the interior of the receptacle 2. More specifically, medical waste is deposited within the interior of the receptacle 2 after it passes into the inlet area; travels through the access opening 120 defined by the rear lateral edge 119, the front lateral edge 121 and upper edges of the side walls 127; and passes through the lower opening defined by the lateral edge 144 of the front slide surface 142 and the lower edges of the side walls 127.

The rear slide 130 and the front slide 140 are configured such that the rear slide surface 132 is axially spaced from the front second slide surface 148 in non-overlapping relation. A plane S1 parallel to the central axis CA and extending through the rear lateral edge 134 is axially spaced a distance d from a plane S3 parallel to the central axis CA and extending through the front lateral edge 144. The distance d is from 0 inches to approximately 1 inch, with a preferred range from greater than zero inches to about 7/8 inch, and a more preferred range from about 1/8 inch to about 5/8 inch, and a more preferred range from about 1/4 inch to about 1/2 inch. Additionally, a plane S2 extending through the rear lateral edge 134 and the front lateral edge 144 is at an angle a relative to the plane S1. The angle .alpha. is from 0 degrees to approximately 25 degrees, with a preferred range from greater than 0 degrees to about 20 degrees, and a more preferred range from about 2 degrees to about 15 degrees, and a more preferred range from about 5 degrees to about 10 degrees. The distance d and the angle .alpha. are selected to provide a tortuous path entry passage having a desired waste clearance and a desired user inaccessibility.

To close the access opening 120 once the receptacle is filled to a desired level, the cover 110 includes a lid portion 150 configured to cover and close the access opening 120. In the present embodiment, the lid portion 150 is integrally hinged to the body portion 112 along a rear edge 115 of the outer perimeter P of the body portion 112 via straps 153. The lid portion 150 includes a lid surface 152 configured to complement the shape of the access opening 120. In the present embodiment, the lid surface 152 has a rectangular configuration, but other configurations are also possible.

Each strap 153 extends between the lid surface 152 and a respective integral hinge 154 extending along the perimeter P of the body portion 112. To lock the lid portion 150 in the closed position, the lid portion 150 includes one or more locking tabs 156 extending from the lid surface 152. To close the access opening 120, the lid surface 152 is pivoted about the hinges 154 until each locking tab 156 engages in a respective locking bore 136. As illustrated in phantom in FIG. 13, the locking bores 136' may alternatively be provided along the covering surface 114.

The cover 110 is configured such that it can be manufactured utilizing the method described above with respect to cover 10. The mold surfaces will be arranged to provide cavity portions corresponding to the various components of cover 110. Again, the components are configured such that the mold portions may be linearly separated to remove the integrally formed cover 110.

Figure 15:
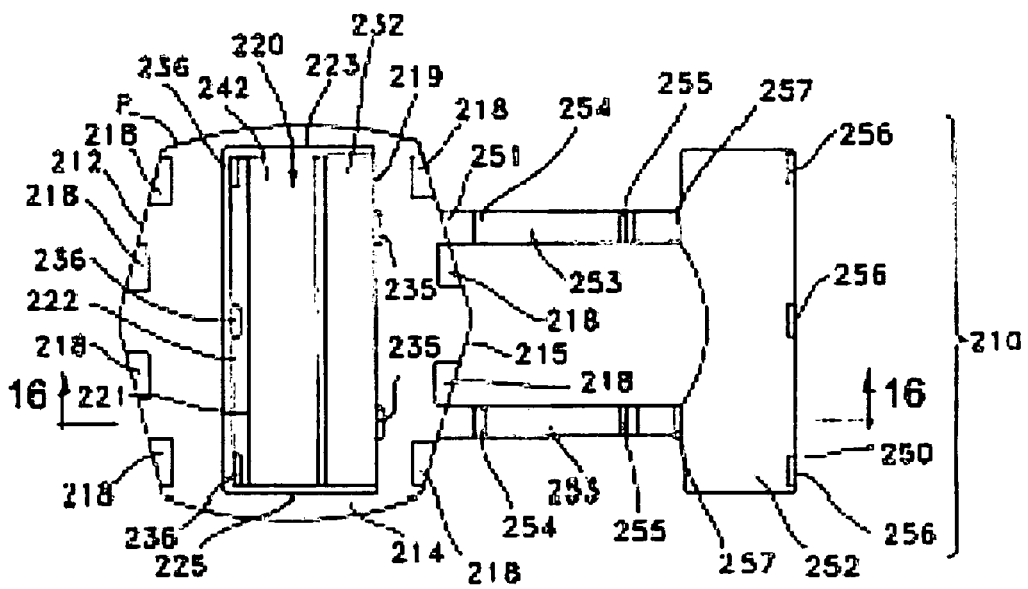
FIG. 15 is a top plan view of a cover that is a third embodiment of the present invention.
Figure 16:
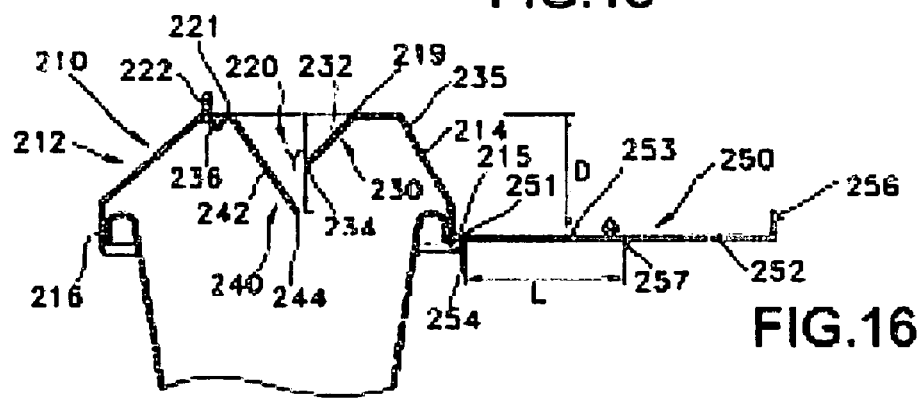
FIG. 16 is a cross-sectional side view along the line 16-16 in FIG. 15.
Figure 17:
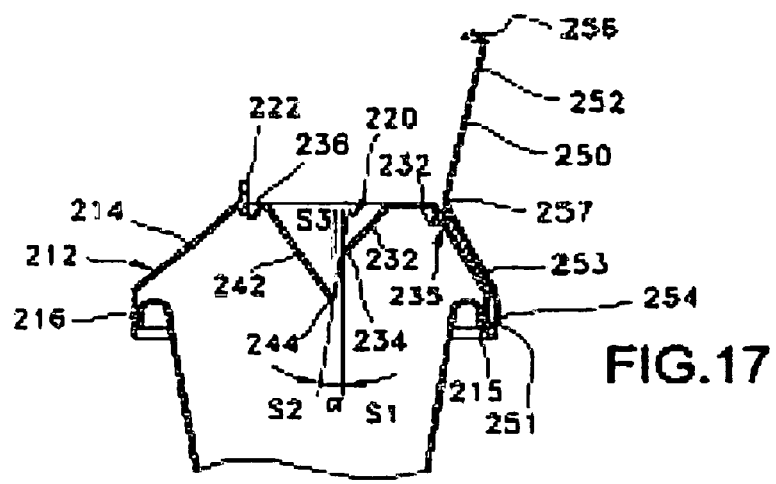
FIG. 17 is a cross-sectional side view similar to FIG. 16 showing the lid portion in an operable position.

Referring to FIGS. 15-17, a cover 210 that is alternate embodiment of the present invention will be described. The cover 210 is similar to cover 10 and cover 110 in that it has a one-piece construction that is capable of being formed using a cost effective molding process. As will be described in detail below, however, the cover 210 differs from cover 10 and cover 110 in the manner in which the lid is coupled to the body portion and in other ways.

The cover 210 includes a body portion 212 and a lid portion 250. The body portion 212 includes a covering surface 214 configured to substantially cover and thereby close a receptacle open end 7. The covering surface 214 has a substantially domed configuration, thereby providing a more pronounced profile as compared to that of covers 10 and 110. Such a profile is optionally provided in order to maximize the capacity of the receptacle 2, to provide steeper slopes at the front and side portions of the cover, and/or to permit a deeper extension of the surfaces defining the covers tortuous path.

The covering surface 214 generally has a configuration that complements the configuration of the receptacle rim 8. In the present embodiment, the covering surface 214 has a chevron shape in both the front and rear portions. The covering surface 214 of the present embodiment has a relatively steep slope such that the body portion 212 is deeper than that of the previous embodiments, as mentioned previously.

A flange 216 depends from at least a portion of the covering surface 214. The body portion 212 is preferably provided with means for securing the cover 210 to a receptacle 2, for example, locking tabs or the like configured to engage the receptacle rim 8. Other securing means may also be utilized.

The body portion 212 has an access opening 220 through the covering surface 214. The access opening 220 is defined by a rear lateral edge 219, a front lateral edge 221 and opposed side edges 223 and 225 extending between the rear and front edges 219, 221. A front wall 222 is provided along the opening front lateral edge 221.

Referring to FIG. 15, a substantially fixed tortuous path extends from the access opening 220 to provide a tortuous entry passage into the receptacle cavity from the access opening 220 which allows for the unrestricted passage of medical instruments and/or waste past stationary surfaces while making hand insertion into the receptacle difficult, if not impossible. In the present embodiment, the tortuous path is defined by a rear slide 230 extending from the opening rear lateral edge 219 and a front slide 240 extending from the opening front lateral edge 221. The rear and front slides 230, 240 are formed integrally with the covering surface 214.

The rear slide 230 includes a sloped rear slide surface 232 terminating along a lateral edge 234. The front slide 240 includes a front slide surface 242 terminating along a lateral edge 244. The front slide surface 242 depends a distance Y from the covering surface 214. The distance Y is preferably less than the depth D of the body portion 212 in order to maintain the slide surface 242 above the interior of the receptacle 2. The rear and front slide surfaces 232 and 242 are substantially planar surfaces, but other configurations are also possible.

The rear slide 230 and the front slide 240 are configured such that the rear slide surface 232 is axially spaced from the front slide surface 242 in non-overlapping relation. A plane S1 parallel to the central axis CA and extending through the rear lateral edge 234 is axially spaced a distance d from a plane S3 parallel to the central axis CA and extending through the front lateral edge 244. The distance d is from 0 inches to approximately 1 inch, with a preferred range from greater than zero inches to about ⅞ inch, and a more preferred range from about ⅛ inch to about ⅝ inch, and a more preferred range from about ¼ inch to about ½ inch. Additionally, a plane S2 extending through the rear lateral edge 234 and the front lateral edge 244 is at an angle .alpha. relative to the plane S1. The angle .alpha. is from 0 degrees to approximately 25 degrees, with a preferred range from greater than 0 degrees to about 20 degrees, and a more preferred range from about 2 degrees to about 15 degrees, and a more preferred range from about 5 degrees to about 10 degrees. The distance d and the angle .alpha. are selected to provide a tortuous path entry passage having a desired waste clearance and a desired user inaccessibility.

The perimeter edge of the access opening 220 is therefore defined by the rear lateral edge 219, the front lateral edge 221 and the upper edge portions of the opposed side edges 223 and 225. Thus, a substantially rectangular access opening 220 (in the embodiment illustrated in FIGS. 15-17) is oriented along a plane that is substantially horizontal but that may be sloped such as toward the rear of the cover 210. A substantially rectangular lower opening is defined by the lateral edge 244 of the front slide surface 242 and the lower edges portions of the opposed side edges 223 and 225. This lower opening is oriented in a plane that is substantially vertical or at an angle to a vertical plane, as will be described later in greater detail.

Medical waste introduced into the tortuous path through the inlet area of the cover 210 follows a circuitous path into the interior of the receptacle 2. More specifically, medical waste is deposited within the interior of the receptacle 2 after it passes into the inlet area; travels through the access opening 220 defined by the rear lateral edge 219, the front lateral edge 221 and upper edge portions of the opposed side edges 223 and 225; and passes through the lower opening defined by the lateral edge 244 of the front slide surface 242 and the lower edges portions of the opposed side edges 223 and 225.

To close the access opening 220 once the receptacle is filled to a desired level, the cover 210 includes a lid portion 250 configured to cover and close the access opening 220. In the present embodiment, the lid portion 250 is integrally hinged to the body portion 212 along a rear edge 215 of the outer perimeter P of the body portion 212 via straps 253. The lid portion 250 includes a lid surface 252 configured to complement the shape of the access opening 220. Each strap 253 extends between the lid surface 252 and a respective integral hinge 254 extending along the perimeter P of the body portion 212 and attached to the body portion at 251.

Due to the deeper nature of the body portion 212 (as compared to body portions 12 and 112 of other cover embodiments), the straps 253 have an extended length with a intermediate locking tab 255 and a secondary hinge 257. To move the lid surface 252 to an operable position, the straps 253 are pivoted about the hinges 254 and the intermediate locking tabs 255 are inserted into intermediate locking bores 235 in the covering surface 214. The straps 253 have a length L that is approximately equal to the depth D of the body portion 212 such that when the locking tabs 255 are locked in the locking bores 235, the hinges 257 are adjacent the top of the body portion 212. As such, to lock the lid portion 250 in the closed position, the lid surface 252 is pivoted about the hinges 257 until each locking tab 256 engages in a respective locking bore 236.

The cover 210 is configured such that it can be manufactured utilizing the method described above with respect to cover 10. The mold surfaces will be arranged to provide cavity portions corresponding to the various components of cover 210. FIG. 15 illustrates bores 218 that may be provided to mold internal components, for example, internal locking tabs (not shown). Again, the components are configured such that the mold portions may be linearly separated to remove the integrally formed cover 210.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A cover for a medical waste disposal receptacle having an open end, the cover comprising a body including a covering surface sized and shaped to cover the open end of the receptacle except for an access opening extending through the covering surface, the access opening being defined by a front opening edge, a rear opening edge, and opposed side edges extending between the front and rear opening edges, the covering surface including an upwardly extending wall portion positioned proximate the front opening edge and both side opening edges, the covering surface defining an outer perimeter and at least a portion of the covering surface being sloped downwardly from the wall portion to the outer perimeter of the covering surface, the body further including fixed first and second sloped slide surfaces integrally formed with the covering surface adjacent the access opening, wherein the first sloped slide surface of the body has opposed first and second slide surface side edges, the body further including a first support wall extending between the covering surface and the first slide surface side edge and a second support wall extending between the covering surface and the second slide surface side edge, the body further including a plurality of locking tabs and a plurality of apertures, each of said apertures being axially aligned along a vertical axis with one of the locking tabs such that the opening, the tortuous path, the first sloped slide surface, the locking tabs, and the apertures of the cover allow a simple linear separation of mold components when the cover is de-molded during manufacture.

2. The cover according to claim 1, wherein the body includes a lid configured to selectively close the access opening, the lid being hinged to the body by an integrally formed hinge extending along a portion of the outer perimeter.

3. The cover of claim 1, wherein the first and second sloped slide surfaces are axially spaced from each other to define a tortuous path extending from the access opening.

4. The cover according to claim 1, wherein the first sloped slide surface extends to a first lateral edge and the second sloped slide surface extends to a second lateral edge spaced a distance from the first lateral edge.

5. The cover of claim 4, wherein the first and second lateral edges are positioned such that a plane extending through the first and second lateral edges is oriented at an angle within a range from about 0 degrees to about 25 degrees relative to the longitudinal axis of the receptacle.

6. The cover according to claim 4, wherein the first and second lateral edges are positioned such that a plane extending through the first and second lateral edges is oriented at an angle within a range from about 0 degrees to about 20 degrees relative to the longitudinal axis of the receptacle.

7. The cover according to claim 4, wherein the first lateral edge is spaced a greater distance from the covering surface than the second lateral edge.

8. The cover according to claim 4, wherein the second lateral edge is spaced a greater distance from the covering surface than the first lateral edge.

9. The cover according to claim 4, wherein the distance between the first lateral edge and the second lateral edge is within a range from about 0 inch and about 1 inch.

10. The cover according to claim 4, wherein the distance between the first lateral edge and the second lateral edge is within a range from about 0 inch and about ⅞ inch.

11. The cover according to claim 1, wherein the body includes a front edge and a rear edge, the first sloped slide surface being closer to the rear edge of the body and the second sloped slide surface being closer to the front edge of the body.

12. The cover according to claim 11, wherein the access opening defines a planar opening sloped toward the rear edge of the body.

13. The cover according to claim 1, wherein the first sloped slide surface extends to a first lateral edge and the second sloped slide surface extends to a second lateral edge, the second lateral edge being axially spaced from the first lateral edge, the first and second lateral edges and the first and second support walls defining a substantially rectangular lower opening spaced from the access opening and oriented at an angle relative thereto.

14. The cover according to claim 1, further including a lid hingedly connected to the body proximate the rear opening edge, the lid configured for movement between an open position and a closed position, the wall and the lid defining a funnel extending towards the access opening when the lid is in an open position.

* * * * *